United States Patent
Morrissette et al.

(10) Patent No.: US 12,048,776 B2
(45) Date of Patent: Jul. 30, 2024

(54) POROUS MATERIAL AND PROCESS

(71) Applicant: GROUPE PPD INC., Waterville (CA)

(72) Inventors: Daniel Morrissette, Sherbrooke (CA); Vincent Morrissette, Sherbrooke (CA)

(73) Assignee: GROUPE PPD INC., Waterville (CA)

( * ) Notice: Subject to any disclaimer, the term of this patent is extended or adjusted under 35 U.S.C. 154(b) by 0 days.

(21) Appl. No.: 16/681,204

(22) Filed: Nov. 12, 2019

(65) Prior Publication Data

US 2020/0147261 A1  May 14, 2020

Related U.S. Application Data

(60) Provisional application No. 62/758,833, filed on Nov. 12, 2018.

(51) Int. Cl.
| | | |
|---|---|---|
| *A61L 27/56* | (2006.01) | |
| *A61K 9/00* | (2006.01) | |
| *A61L 27/18* | (2006.01) | |
| *A61L 27/44* | (2006.01) | |
| *A61L 27/54* | (2006.01) | |

(52) U.S. Cl.
CPC .............. *A61L 27/18* (2013.01); *A61L 27/44* (2013.01); *A61L 27/54* (2013.01); *A61L 27/56* (2013.01); *A61L 2400/08* (2013.01)

(58) Field of Classification Search
CPC .... A61F 2002/3092; A61F 2002/30593; A61F 2002/30784; A61F 2002/30772; A61L 27/56; A61L 2430/02; A61L 31/146; A61L 24/0036; A61L 15/425; A61L 27/48; A61L 31/14; A61L 31/12; A61L 29/146; A61K 9/0024; A61K 8/0283; A61K 8/0279; A61K 8/0216; A61K 8/0233; A61K 9/0092
See application file for complete search history.

(56) References Cited

U.S. PATENT DOCUMENTS

| | | | |
|---|---|---|---|
| 3,992,725 A | 11/1976 | Homsy | |
| 8,383,024 B2 | 2/2013 | Morrissette et al. | |
| 8,770,500 B2 | 7/2014 | Mukhopadhyay et al. | |
| 8,829,096 B2 | 9/2014 | Jarman-Smith | |
| 9,011,963 B2 | 4/2015 | Osterwalder et al. | |
| 9,085,665 B1 | 7/2015 | Chang et al. | |
| 9,353,235 B1 | 5/2016 | Chang et al. | |
| 9,498,922 B2 | 11/2016 | Chang et al. | |
| 9,504,550 B2 | 11/2016 | Chang et al. | |
| 9,517,593 B2 | 12/2016 | Chang et al. | |
| 9,622,847 B2 | 4/2017 | Chang et al. | |
| 9,764,502 B2 | 9/2017 | Chang et al. | |
| 9,848,973 B2 | 12/2017 | Chang et al. | |
| 9,855,709 B2 | 1/2018 | Chang et al. | |
| 9,908,296 B2 | 3/2018 | Chang et al. | |
| 10,226,883 B2 | 3/2019 | Chang et al. | |
| 10,405,962 B2 | 9/2019 | Chang et al. | |
| 2008/0075752 A1 | 3/2008 | Ratner et al. | |
| 2009/0222091 A1* | 9/2009 | Morrissette | B32B 27/00 623/17.11 |
| 2010/0255053 A1* | 10/2010 | Savage-Erickson | A61L 27/12 424/423 |
| 2012/0288441 A1* | 11/2012 | O'Gara | A61P 43/00 514/772.3 |
| 2012/0323339 A1 | 12/2012 | Olalde Graells et al. | |
| 2017/0071717 A1 | 3/2017 | Chang et al. | |
| 2017/0112959 A1 | 4/2017 | Erbe et al. | |
| 2018/0193126 A1 | 7/2018 | Chang et al. | |

FOREIGN PATENT DOCUMENTS

| | | |
|---|---|---|
| CA | 2785571 | 6/2011 |
| CA | 2799196 | 6/2015 |
| CA | 2799211 | 6/2015 |
| CA | 2704697 | 3/2016 |
| EP | 950421 A1 | 10/1999 |
| JP | 2009-514996 A | 4/2009 |
| JP | 2013-526932 A | 6/2013 |
| WO | 2017205835 | 11/2017 |

OTHER PUBLICATIONS

Abdur R. Siddiq, Andrew R. Kennedy, "Porous Poly Ether Ketone (PEEK) manufactured by a novel powder route using near-spherical salt bead porogens: Characterisation and mechanical properties".

* cited by examiner

*Primary Examiner* — Tracy Liu
(74) *Attorney, Agent, or Firm* — LAVERY, DE BILLY, LLP; Hugh Mansfield

(57) ABSTRACT

A porous material suitable for implant is disclosed comprising a large plurality of substantially spherical intercalated hollows in a polymer. The hollows are formed by combining the polymer with a fugitive material under heat and pressure and subsequently removing the fugitive material to reveal the hollows. Intercalation can be increased by subjecting the fugitive material to a coalescing compacting process prior to combining the fugitive material with the polymer. The porous material can be combined with a solid material such as a solid polymer to fabricate complex implantable materials with a variety of features.

13 Claims, 6 Drawing Sheets

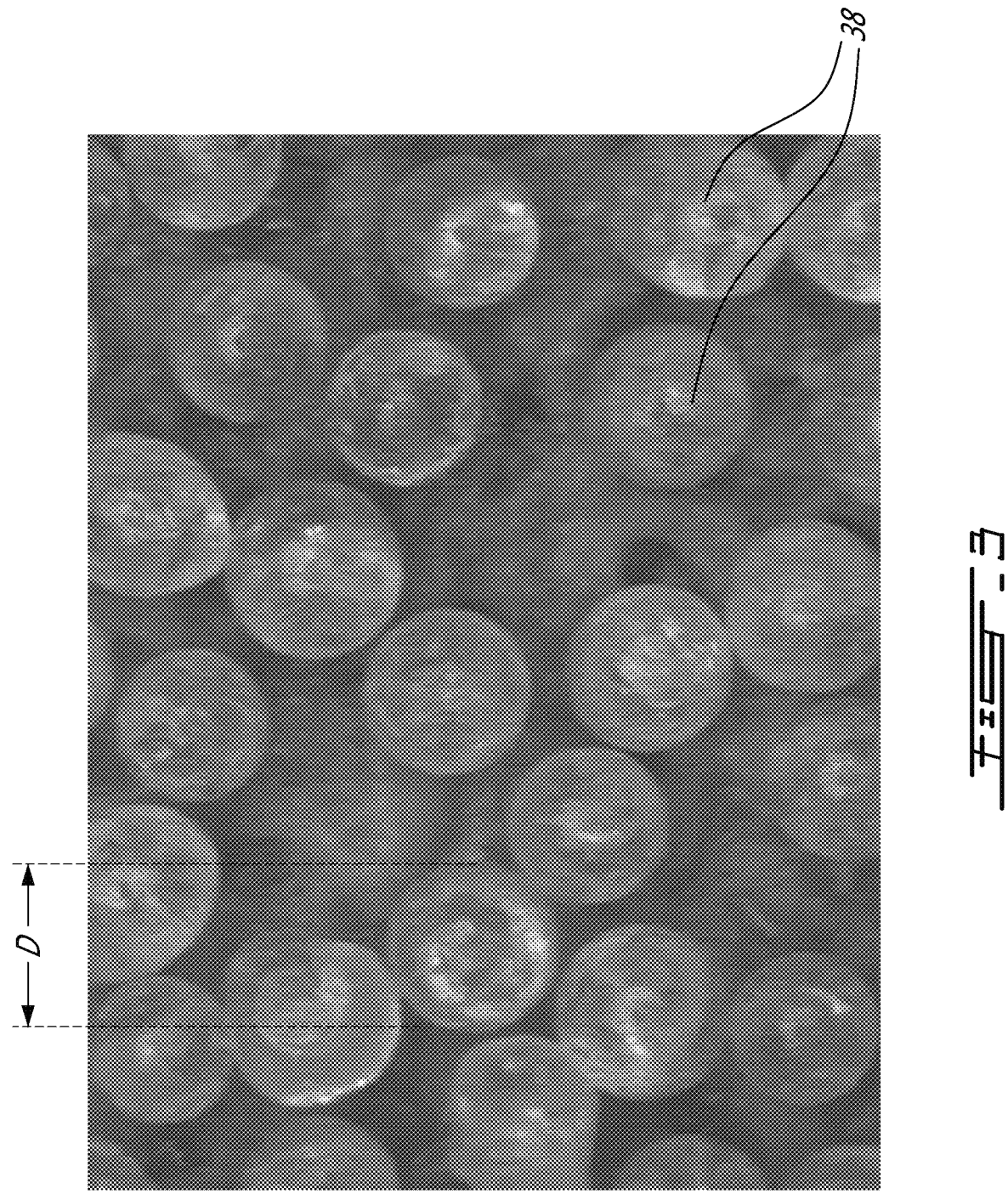

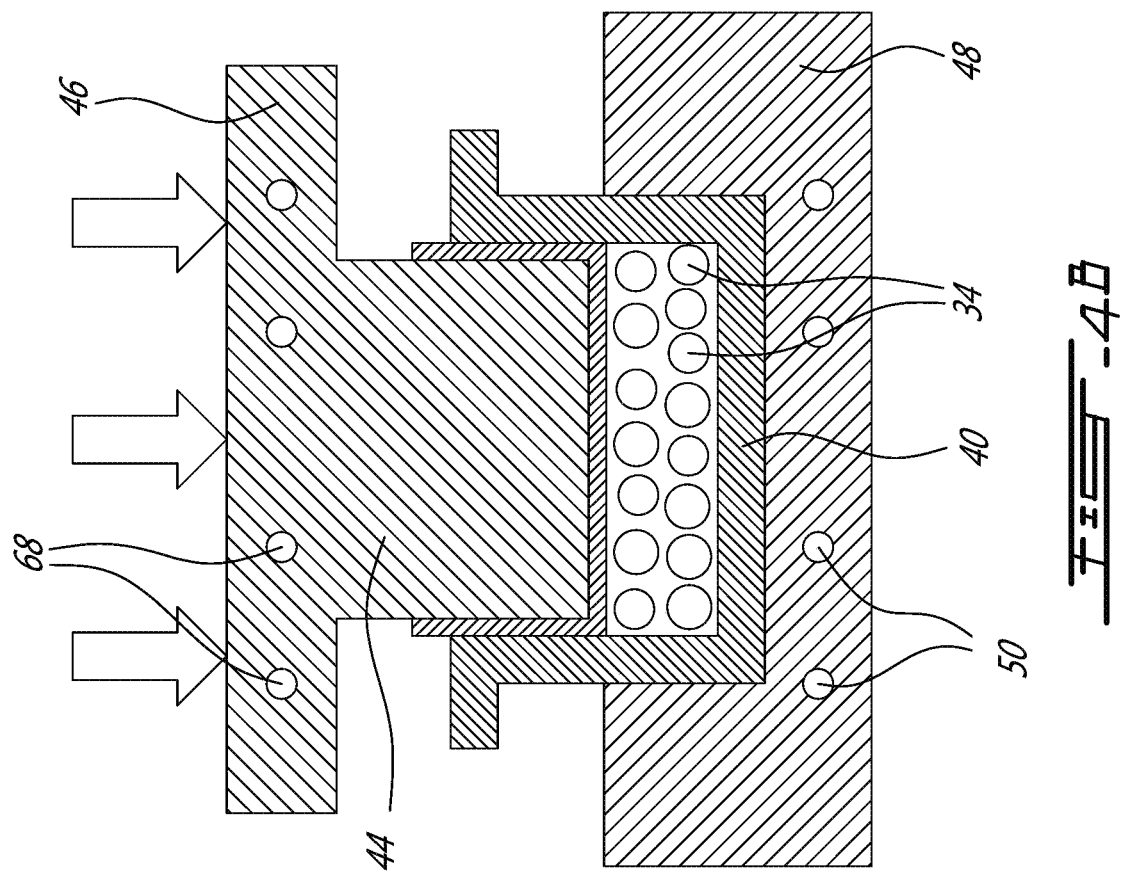
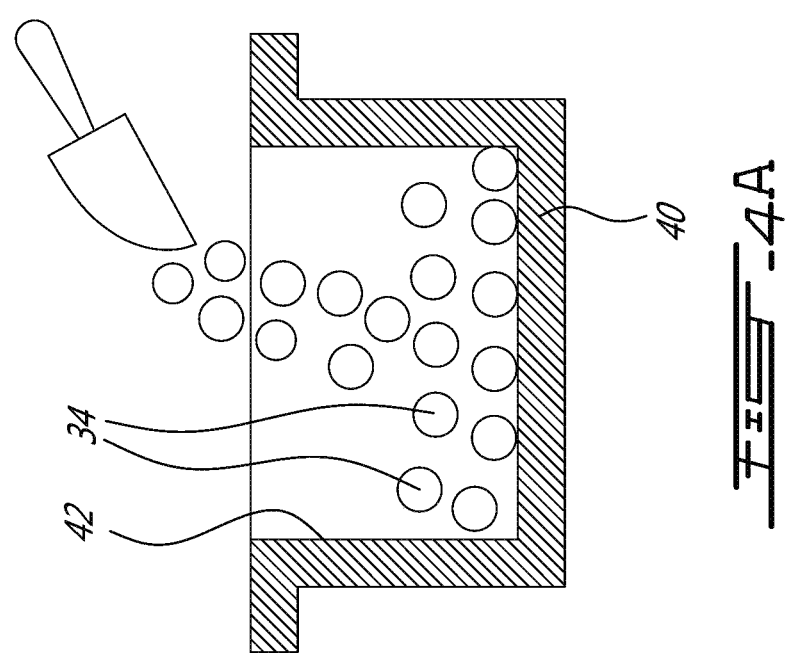

POROUS MATERIAL AND PROCESS

CROSS REFERENCE TO RELATED APPLICATIONS

This application claims benefit, under 35 U.S.C. § 119(e), of U.S. provisional application Ser. No. 62/758,833 filed on Nov. 12, 2018, which is incorporated herein in its entirety by reference.

FIELD OF THE INVENTION

The present invention relates to a porous material and a method for fabricating the same. In particular, the present invention relates to a porous polymer suitable for implant and a method for fabricating same.

BACKGROUND OF THE INVENTION

A variety of methods exist in the art for forming porous micro-plastic materials. In particular, the prior art discloses producing a porous product by mixing a salt-type pore-forming agent such as sodium chloride to a resin to form a molding material, subjecting the molding material to a molding process to produce a molded part and subsequently washing the product to elute or leach the salt-type pore forming agent, thereby forming pores. The prior art also teaches methods for producing such porous structures using spherical or rounded salt particles. However, due to their spherical nature, these spherical salt particles only make contact with each other at their diametrical edges, resulting in poor interconnectivity of the pores in the porous material.

SUMMARY OF THE INVENTION

In order to address the above and other drawbacks, there is provided a material suitable for implant comprising a rigid biocompatible polymer comprising a plurality of interconnected hollows; wherein substantially all of said hollows are spherical and substantially all of said hollows have a diameter of between 180 µm and 600 µm and further wherein less than 50% of a volume comprises said biocompatible polymer.

There is also provided a material suitable for implant comprising a solid part comprising a solid biocompatible polymer; and a porous part comprising a rigid biocompatible polymer comprising a plurality of interconnected hollows wherein substantially all of said hollows are spherical and wherein substantially all of said hollows by volume have a diameter of between 180 µm and 600 µm and further wherein less than 50% of a volume of said porous part comprises said biocompatible polymer.

Additionally, there is provided an intermediate material for fabricating an implant comprising a rigid biocompatible polymer and a fugitive material suspended in said polymer and consisting essentially of partially flattened spherical particles.

Also, there is provided a method for fabricating a porous implant. The method comprises placing a quantity of inelastic particles of a fugitive material in a mold; heating said mold to a first temperature while applying a first mechanical pressure to partially flatten said inelastic particles; placing a biocompatible polymer in said mold together with said partially flattened particles; heating said mold to a second temperature while applying a second mechanical pressure to form a mixture of said biocompatible polymer and said partially flattened particles; and removing said partially flattened particles from said mixture. An amount of said partially flattened particles relative to the polymer is present such that removal of said partially flattened particles from said mixture leaves a resultant porous material comprising the polymer and a plurality of interconnected hollows.

Furthermore, there is provided an intermediate material for subsequent use in producing a porous material suitable for implant. The intermediate material consists essentially of a mass of substantially spherical coalesced particles.

BRIEF DESCRIPTION OF THE DRAWINGS

FIGS. 1A and 1B provide respectively a plan view of a porous material in accordance with an illustrative embodiment of the present invention and a CT scanned image of a porous material in accordance with an illustrative embodiment of the present invention;

FIG. 3 provides a plan view of a fugitive material in accordance with an illustrative embodiment of the present invention;

FIGS. 4A and 4B provide sectional views of respectively a mold filled with a fugitive material and a molding assembly compressing a fugitive material in accordance with an illustrative embodiment of the present invention.

DETAILED DESCRIPTION OF THE ILLUSTRATIVE EMBODIMENTS

Figure 1A:
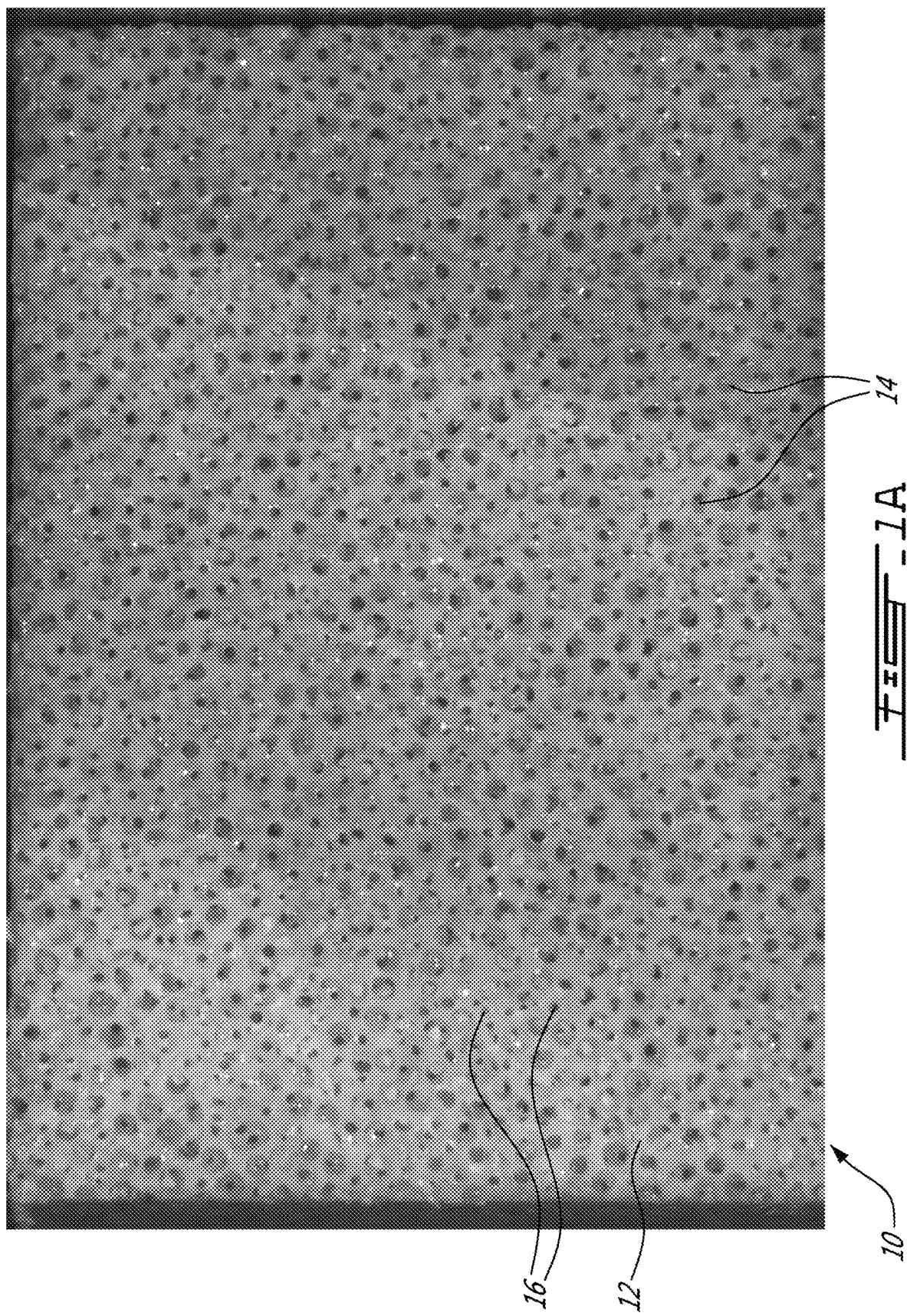

Referring now to FIGS. 1A and 1B, a material suitable for implant, and generally referred to by the reference numeral 10, will be described. The material 10, comprises a porous biocompatible polymer 12 comprising a large plurality of spherical hollows 14 therein. The hollows 14 are substantially similar diameter, for example between 300 µm and 415 µm and are interconnected with each of a plurality of other hollows 14 by an aperture 16. Each aperture 16 is of similar size and substantially circular in shape. Additionally, spacing between the hollows 14 is such that the biocompatible polymer 12 occupies at most between 15% and 50% which might be otherwise occupied by the material 10.

Figure 2:
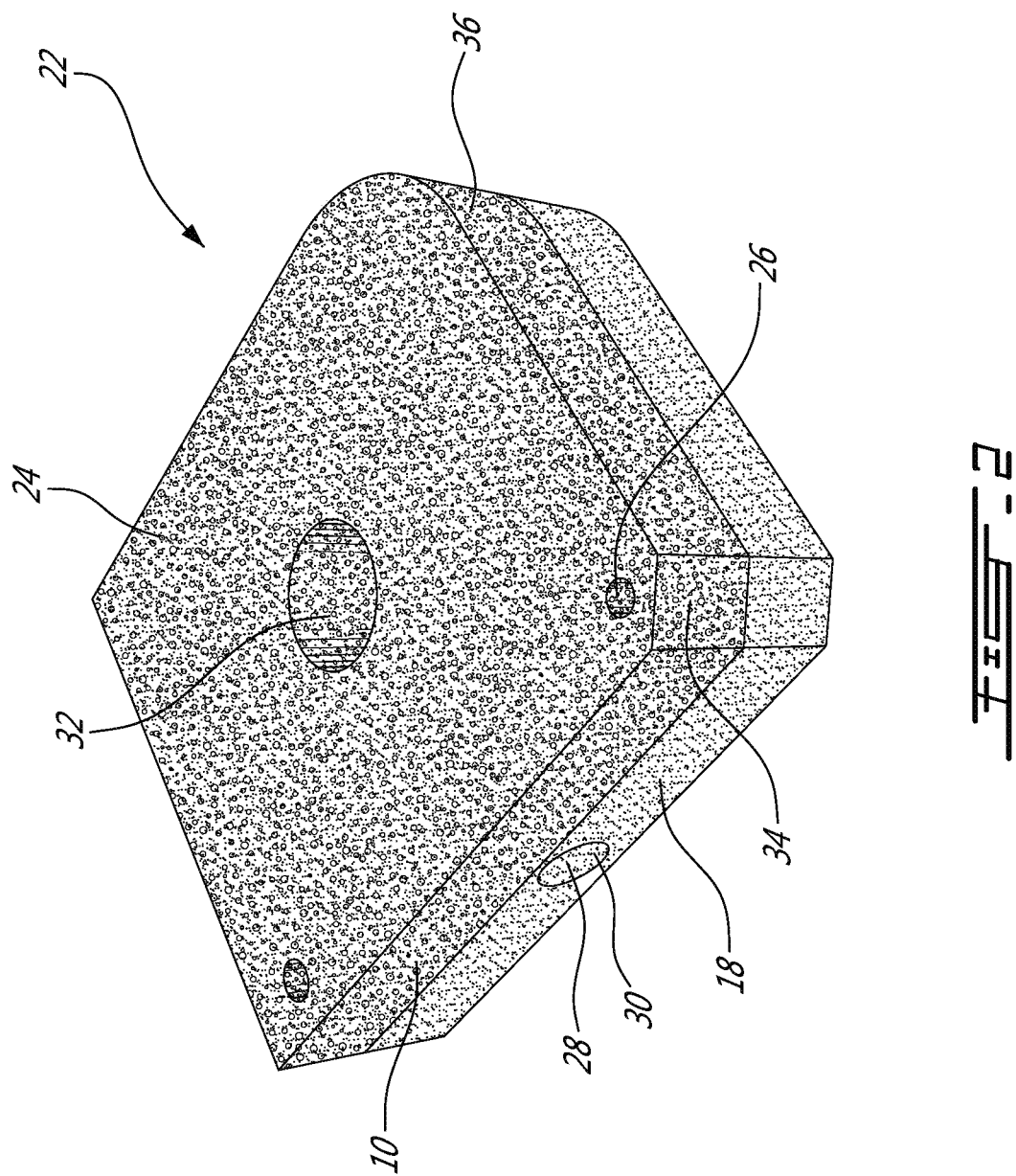
FIG. 2 provides a perspective view of porous biocompatible material combined with a solid biocompatible material in accordance with an illustrative embodiment of the present invention.

Referring to FIG. 2, in a particular embodiment the porous biocompatible material 10 can be combined with a solid biocompatible material 18 to form a composite blank 20. The composite part blank 20 can be machined to provide an implant 22, for example using a CNC milling machine (not shown) or the like, to expose the porous surface 24 of the porous material 12 and introduce various features such as perforations 26, for example for receiving alignment pins (not shown) or the like, bores 28 which can comprise a thread 30, for example for receiving fasteners such as screws (not shown) or the like, apertures 32, bevelled edges 34 and contoured surfaces 36.

Referring back to FIG. 1A in addition to FIG. 2, in a particular embodiment the hollows 14 can be filled with a material which promotes bone ingrowth, for example a bioglass (not shown) or the like, either during the fabrication of the porous biocompatible polymer 12 or subsequently via the exposed porous surface 24 following machining of the implant 22. In another embodiment, the hollows can be filled with a bioactive agent, such as bioglass or the like, which is displaceable after implant by a biological process.

Referring to FIG. 3 in addition to FIG. 1A, in one embodiment the porous material 12 is fabricated from a polymer such as polyether ether ketone (PEEK) and a fugitive material 34 substantially all of which is spherical with few non-spherical particles. While in an illustrative embodiment the polymer described herein comprises a poly aryl ether ketone such as PEEK and the fugitive material comprises a sodium chloride salt, in a given embodiment other suitable materials may be used. The method comprises four (4) main steps: spherization of the fugitive material, molding of the spherical fugitive material together with the polymer to produce an intermediate part, machining of the part intermediate part to reveal porous surfaces and introduce features, and removal of the fugitive material from the machined part to form the implant.

Still referring to FIG. 3, the fugitive material is illustratively comprised of a large plurality of spherical particles 34 each comprising a similar diameter D. In an illustrative embodiment the preferred diameter D is within a range of 300 μm and 600 μm, in particular with about at least $\frac{1}{3}^{rd}$ of the spherical particles between 300 μm and 400 μm and about at least $\frac{1}{3}^{rd}$ of the particles between 400 μm and 600 μm with the remainder outside of these ranges. In a particular embodiment between about 5% and about 20% of the spherical particles are outside of the range of 300 μm and 600 μm. As will be discussed in more detail below other ranges or combinations of ranges may be used in a given embodiment and to aid in achieving, inter alia, a particular porosity (i.e. the ratio of resultant hollow space to polymer once the fugitive material has been removed) or intercalation.

Still referring to FIG. 3, as discussed above, in an illustrative embodiment the fugitive material is a NaCl salt. NaCl salt particles of irregular shape are sifted into groups comprising salt particles of different sizes. Illustratively a four-stage sifter can be used to separate salt into various size ranges. In an embodiment, a sifting device may allow for the sorting of four (4) size ranges. Illustratively, a first sifter allows for the collection of 716 μm to 583 μm salt particles, a second sifter allows for the collection of 582 μm to 471 μm salt particles, a third sifter allows for the collection of 470 μm to 311 μm salt particles, and a fourth sifter allows for the collection of salt particles of less than 310 μm.

Still referring to FIG. 3, at a subsequent step a selected range of salt particles are subject to a spherization process using a spherization assembly (not shown) to produce quantities of spherical salt particles. The spherization assembly supports implementation of a process that imparts a physical modification to the particles of salt from an irregular form to spherical.

Still referring to FIG. 3, salt particles 38 of a selected range are agitated and entrained along a conduit (not shown) by compressed air and traverse an oven (also not shown) wherein the salt particles 38 are heated. The air ensures that the flow of salt particles 38 is well separated for spherization purposes. As the heated salt particles 38 exit the conduit, the heated salt particles 38 are further heated in a flame (also not shown), for example from a blowtorch or the like, which renders the substantially spherical fugitive material 34. The spherical fugitive material 34 is subsequently cooled and collected.

Still referring to FIG. 3, the combination of heating, agitation and subsequent cooling of the salt particles 38 results in the desired spherical fugitive material 34. The spherical fugitive material 34 is collected and illustratively subject to additional sifting through a sifting device (not shown) and then sorted into ranges. Illustratively, the spherical fugitive material 34 is sorted into the following size ranges: 180 μm to 300 μm, 300 μm to 425 μm, 425 μm to 500 μm, 500 μm to 600 μm, and >600 μm.

Referring now to FIGS. 4A and 4B, following spherization, the spherical fugitive material 34 is placed in a mold 40 defining a cavity 42 which is subsequently closed with a tight fitting mold cap 44. A piston (not shown) drives an upper plate 46 towards a lower plate 48 and thus the mold cap 44 into the cavity 42. Controlled heating of the mold cavity 42 and the mold cap 44 is provided for example via a plurality of electrical heating elements 50. Additionally, controlled cooling of the mold cavity 42 and the mold cap 44 is provided for example through cavities (not shown) in both the upper plate 46 and the lower plate 48 through which a cooling fluid such as water may be circulated. Temperatures within the mold cavity 42 are detected via thermocouples (also not shown) mounted proximate to the lower end of the mold cavity 42. Furthermore, the actual mechanical pressure applied between the upper plate 46 and the lower plate 48 by the piston can be detected by means of a load cell (also not shown). By including independent heating elements 50, cooling cavities as well as a plurality of thermocouples, the upper plate 46, and thus the mold cap 44, can be heated and cooled independently of the lower plate 48, and thus the mold cavity 42, which ensures accurate control of the temperature of the materials within the mold cavity 42. Although the piston is preferably driven by an electric actuator (not shown), other types of actuators, such as hydraulic or compressed air, may be suitable in certain applications. Additionally, although heating and cooling of the upper plate 46 and the lower plate 48 is illustratively provided by electrical heating and water cooling, respectively, other means of heating and cooling the mold 40, such as Peltier effect devices (not shown) or the like, may be provided with appropriate modifications to the assembly.

Still referring to FIGS. 4A through 4B, in order to, inter alia, increase the interconnectivity of the hollows in the porous material, the spherical fugitive material 34 placed in the mold cavity 42 are first subject to a compression and heating process. In this regard, with the spherical fugitive material 34 in the mold cavity 42 the piston is actuated such that the upper plate 46 is lowered towards the lower plate 48 and the mold cap 44 is driven into the mold cavity 42. Of note, the mold cap 44 and mold cavity 42 may take on a number of simple or complex forms, thereby allowing materials to be formed for subsequent machining or parts with a variety of molded shapes. While this compressing occurs, current is applied to the electrical heating elements 50 in order to heat the mold 40 and thus the spherical fugitive material 34 illustratively to 280° C. Once the desired temperature is achieved, additional pressure is applied, illustratively up to 1.37 Mpa.

Still referring to FIGS. 4A through 4B following application of pressure under heating the spherical fugitive material 34 is illustratively partially flattened and largely coalesced. Typically, on opening the mold at this stage the partially flattened and coalesced spherical fugitive material 34 can be removed in one piece, or a small number of large pieces each comprising a large plurality of the partially flattened spherical fugitive material 34. In any case, upon opening the mold 40 the partially flattened and coalesced spherical fugitive material 34 does not disintegrate but rather retains its structure when subject to subsequent process steps.

Figure 5C:
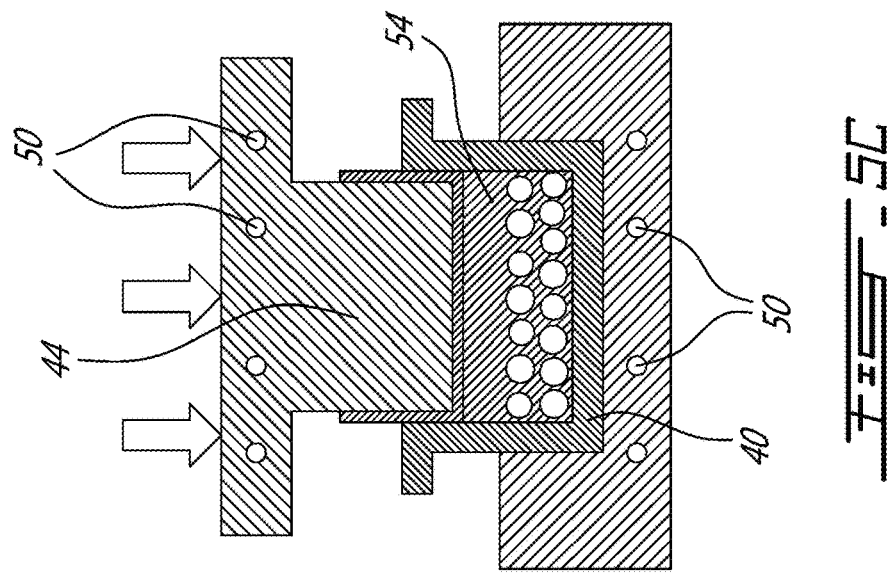
FIGS. 5A, 5B and 5C provide sectional views of respectively a mold filled with a compressed fugitive material and PEEK, a molding assembly compressing a compressed fugitive material and PEEK and a molding assembly following compression a compressed fugitive material and PEEK in accordance with an illustrative embodiment of the present invention.
Figure 5B:
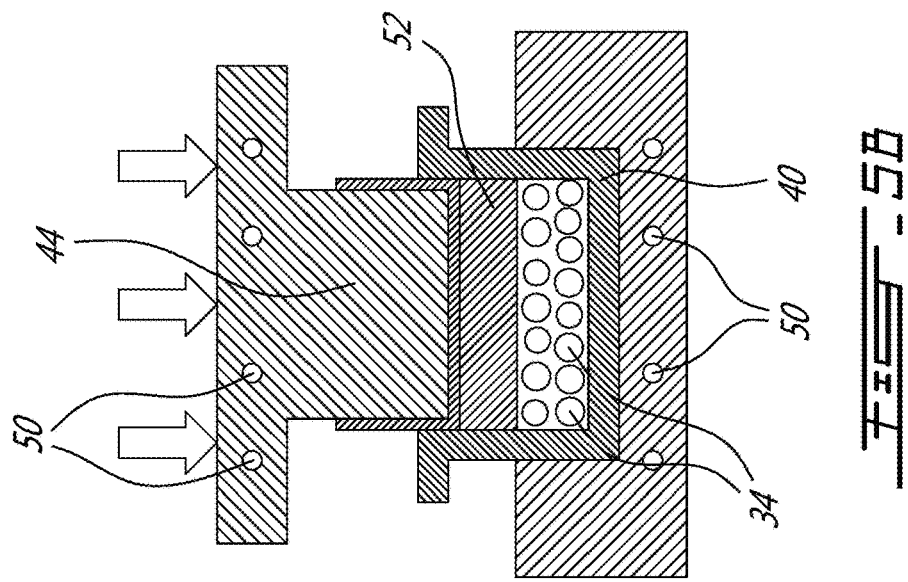
Figure 5A:
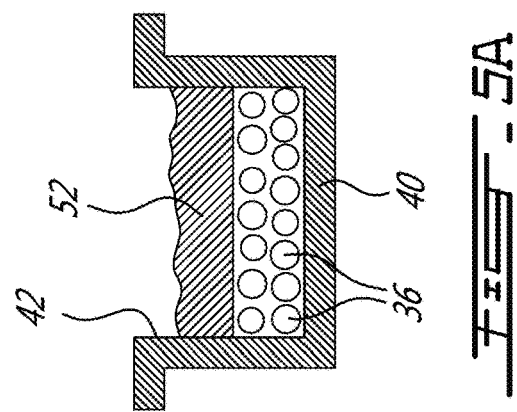

Referring now to FIGS. 5A through 5C, in an illustrative embodiment following compression, the mold 40 is opened and a layer of PEEK 52 is placed over the partially flattened and coalesced spherical fugitive material 34. The mold cavity 42 is again closed by the mold cap 44 and the PEEK 52 is compressed into the partially flattened fugitive material 34 while heat is applied via the heating elements 50 to heat the mold 40, illustratively to 400° C., and to form an intermediate material 54 comprising a mixture of PEEK 52 and partially flattened fugitive material 34. The duration of the melting phase is dependent on a number of factors including the quantity and depth of intermediate material 54 within the mold 40. Once the desired temperature is achieved, additional pressure is applied, illustratively circa 3.45 Mpa, while the intermediate material comprising a mixture of PEEK 52 and fugitive material 34 is allowed to cure. At the end of the heating and curing phases, the heating elements 50 are deactivated and the cooling phase begins. During the cooling phase, a high pressure, illustratively circa 6.9 Mpa, is applied by the piston to the intermediate material via the mold cap 44 and a cooling fluid such as water is circulated within the cavities, thereby cooling the mold 40 and thus the intermediate material 54. Once the intermediate material 54 has adequately solidified, the piston is actuated to retract the mold cap 44 from the mold cavity 42, thereby allowing the molded intermediate material 54 to be removed from the mold cavity 42.

As discussed above, and with reference back to FIG. 2, the porous structure may be subsequently machined. In some cases machining is optional, and in some embodiments an implantable part may be arrived at without any machining. Further, machining may be carried out after removal of the fugitive material 34 rather than before. A person of skill in the art would understand that a variety of machining techniques can be used to obtain the desired structure of a part or parts comprising the porous structure. PEEK lends itself well to machining, allowing porous PEEK parts such as those fabricated according to the present invention to be shaped using a variety of cutting tools.

In order to remove the fugitive material in the form of spherical particles 34, the solidified molded mixture 54 is placed in an ultrasonic bath (not shown) containing a solvent such as heated distilled water. Illustratively, the water is heated to 70° C. The solidified molded mixture 54 is soaked in the bath until the salt has been dissolved from the mixture 54, thereby revealing a porous material with intercalated hollows. The solidified molded mixture 54 is retained in the bath for a period of time that is dependent on its volume. The porous material is then removed from the bath and allowed to dry in a dryer (not shown), for example overnight and at 100° C. Finally, the finished porous material is removed from the dryer. The resultant porous PEEK material is suitable for implants, with the interconnected hollows promoting bone in growth.

In order to improve the strength of the yielded porous part, annealing techniques can be used. Typically, the annealing techniques used are supplied by the manufacturer of the raw materials.

With reference back to FIGS. 5A through 5C in addition to FIG. 2, in an alternative embodiment, an additional layer of PEEK 52 can be placed in the bottom of the mold 40, or on top of the PEEK/salt mixture 54, in order to form a solid PEEK/porous PEEK composite. In this regard, the solid layer acts as a barrier between the porous layer and other parts and may be used, for example, to limit bone in growth into the resultant molded part. Additionally, as discussed above, PEEK lends itself well to machining, and as a result the solid layer can be machined, for example for interconnection with other parts fabricated from PEEK or other materials, such as titanium, tantalum or the like. Alternatively, other PEEK composite materials such as PEEK reinforced with carbon (e.g. PEEK carbon prepreg or pre-impregnated fibers) or other fibers can be molded together with the PEEK/salt admixture to provide composite structures having a variety of different characteristics in terms of strength, stiffness, flexibility and the like, thereby making the resultant composite suitable for a wide variety of applications. Additionally, a multilayered solid/porous composite can be formed by alternating layers of PEEK or PEEK composites and PEEK/salt mixture.

In another alternative illustrative embodiment, the method of the present invention can be applied more generally using materials other than PEEK and table salt. Indeed, as will now be understood by persons of ordinary skill in the art, the present invention can be applied to virtually any first material which is in a liquid or fluid form at a temperature below the melting point of the second particulate material and which is subsequently able to harden to form a solid composite. Of course, the second particulate material must also be able to be removed from the solid composite to leave the porous structure of the hardened first material.

In still another alternative illustrative embodiment the method of the present invention can be applied more generally to a first material in a liquid form at room temperature, such as an epoxy or other polymer, which subsequently hardens following mixing with a second solid particulate material through the introduction of a catalyst hardener or the like. A similar result can be arrived at with first materials which may be heat set, or cured, through the application of heat and pressure.

Although the present invention has been described hereinabove by way of specific embodiments thereof, it can be modified, without departing from the spirit and nature of the subject invention as defined in the appended claims.

The invention claimed is:

1. A material suitable for implant comprising:
   a porous rigid biocompatible polymer formed by a process comprising compressing spherical particles to render partially flattened spherical particles, combining a biocompatible polymer with said partially flattened spherical particles to form a composite and subsequently removing the partially flattened spherical particles from the composite to leave a plurality of partially flattened interconnected hollows.

2. The material suitable for implant of claim 1, wherein between 50% and 15% of the volume of the material comprises said biocompatible polymer.

3. The material suitable for implant of claim 1, wherein said plurality of partially flattened interconnected hollows have a diameter of between 315 μm and 425 μm.

4. The material suitable for implant of claim 1, wherein the material can withstand a pressure of at least 20 Mpa.

5. The material suitable for implant of claim 1, wherein each of said partially flattened hollows is filled with a bioactive agent, said bioactive agent is displaceable after implant by a biological process.

6. The material suitable for implant of claim 5, wherein said bioactive agent comprises a bio glass.

7. A material suitable for implant comprising:
   a solid part comprising a solid biocompatible polymer; and a porous part comprising a rigid biocompatible polymer formed by a process comprising compressing spherical particles to render partially flattened spherical particles, combining a biocompatible polymer with said partially flattened spherical particles to form a composite and subsequently removing the partially flattened spherical particles from the composite to leave a plurality of partially flattened interconnected hollows.

8. The material suitable for implant of claim 7, wherein all of said partially flattened hollows have a diameter of between 315 μm and 425 μm.

9. The material suitable for implant of claim 1, wherein each of said partially flattened hollows is interconnected with a plurality of adjacent partially flattened hollows by a circular aperture.

10. The material suitable for implant of claim 1, wherein all of said partially flattened hollows have a diameter of between 180 μm and 600 μm.

11. The material suitable for implant of claim 1, wherein 50% or less of a volume of the material comprises said biocompatible polymer.

12. The material suitable for implant of claim 7, wherein all of said partially flattened hollows have a diameter of between 180 μm and 600 μm.

13. The material suitable for implant of claim 7, wherein 50% or less of a volume of said porous part comprises said biocompatible polymer.

\* \* \* \* \*